United States Patent
Errey et al.

(10) Patent No.: US 7,431,742 B2
(45) Date of Patent: Oct. 7, 2008

(54) HAIR COLORING KITS AND METHODS OF USE THEREOF

(75) Inventors: Pauline Jane Errey, New Canaan, CT (US); Christine Lee Haas, New York, NY (US); Vera Hille, Barnes (GB); Tracy Stephens, Bracknell (GB)

(73) Assignee: The Procter & Gamble Company, Cincinnati, OH (US)

( * ) Notice: Subject to any disclaimer, the term of this patent is extended or adjusted under 35 U.S.C. 154(b) by 249 days.

(21) Appl. No.: 11/413,823

(22) Filed: Apr. 28, 2006

(65) Prior Publication Data

US 2007/0251025 A1 Nov. 1, 2007

(51) Int. Cl.
*A61Q 5/10* (2006.01)

(52) U.S. Cl. .................. 8/405; 8/406; 8/431; 8/435; 8/552; 8/581; 8/632; 132/202; 132/208

(58) Field of Classification Search ............... 8/405, 8/406, 431, 435, 552, 581, 632; 132/202, 132/208

See application file for complete search history.

(56) References Cited

U.S. PATENT DOCUMENTS

2004/0045098 A1 * 3/2004 Lazzeri ................ 8/405

FOREIGN PATENT DOCUMENTS

| DE | 10340695 | A1 | 1/2004 |
|---|---|---|---|
| EP | 1356800 | A2 | 10/2003 |
| EP | 1356801 | A1 | 10/2003 |
| EP | 1356802 | A1 | 10/2003 |
| EP | 1356803 | A1 | 10/2003 |
| EP | 1357143 | A1 | 10/2003 |
| EP | 1358864 | A2 | 11/2003 |
| EP | 1358865 | A2 | 11/2003 |

* cited by examiner

*Primary Examiner*—Eisa B Elhilo
(74) *Attorney, Agent, or Firm*—Melissa Krasovec; Marianne Dressman; Tara M. Rosnell

(57) ABSTRACT

The present invention relates to hair colouring kits and methods of use thereof which comprise an oxidative component, a colouring component, a conditioner component and a colour refresher component. The kits and methods of use thereof allow for the delivery of the required initial colour and shine to the hair but which further enable the maintenance of the colour over a longer time period without the need for an additional oxidative colouring event.

9 Claims, No Drawings

HAIR COLORING KITS AND METHODS OF USE THEREOF

FIELD OF THE INVENTION

The present invention relates to hair colouring kits and methods of use of said kits.

BACKGROUND OF THE INVENTION

The alteration of the colour of keratinous fibres, in particular human hair, by the application of hair dyes is well known. In order to provide the consumer with the hair colour and the intensity of colour desired, a very complex chemical process is utilized. Non permanent hair colourant formulations typically comprise a non permanent dye such as direct dyes and or pigments which are deposited on to the surface of the hair and are gradually washed out over successive washing cycles. Permanent hair colourant formulations typically comprise oxidative hair dye precursors, which can diffuse into the hair through the cuticle and into the cortex where they can then react with each other and suitable oxidising agents to form the end dye molecules. Due to the large size of these resultant molecules they are unable to readily diffuse out of the hair during subsequent washing with water and/or detergents; hence delivering the consumer-desired permanency of colour. The reaction typically takes place in an aggressive environment at approximately pH 8 to 11 in the presence of an alkalizing agent and in the presence of an oxidizing agent. Moreover, the consumer repeats this process regularly in order to maintain the desired hair colour shade and the intensity of colour and to ensure continual, even coverage of the hair including coverage of new hair growth. Hair bleaching and highlighting compositions further typically utilize a strong oxidizing agent such as hydrogen peroxide and a persulphate salt in order to lighten the hair colour.

However, despite the fact that commercial hair colourant products have been available for many years, the products still exhibit a number of consumer-related deficiencies. The initial colour result, obtained immediately after colouring the hair, changes over time during the subsequent days and weeks resulting in both a change in colour intensity and shine, and colour tonality of the hair. Whilst not wishing to be bound to theory, this change in colour is thought to be exaggerated when the hair is in poor condition. Hair which has been permanently coloured typically has a poor condition, which manifests itself in the presence of a hydrophilic surface and chemical damage to hair proteins caused by the chemical process of colouring, and poorer cuticle integrity. This poor condition increases during the interval between hair colouring events. Further to the impact of enhancing the change of colour and shine during the time period in between colouring events, the poor condition of the hair leads to an increased difficulty of detangling, combing and styling the hair.

Many attempts have been made to improve the colour and damage profile of hair colourants. These have typically resided in the development of new dye precursors, and combinations of dye precursors to enhance the so called "wash-fade" profile. Despite offering some advantages, this approach does not provide sufficient advantages in colour maintenance overtime, and is not effective for all desired shades. Alternatively, the use of oxidative dyes in combination with pre-formed direct dyes within a single composition or as separate application steps has been taught. Such products may yield more intense initial colour, but without however the long term desired colour profile and with unacceptable variations in root to tip colour uptake and hair condition.

Durable silicone conditioner treatment compositions have been described in the following publications: EP1356802, EP1356803, EP1358865, EP1357143, EP1356801, EP1356800 and EP1358864 to improve the condition of hair over the time period in between colouring events. However the problem of colour maintenance is not addressed.

Attempts have also been made to "seal" in the delivered colour by improving the hair condition. Whilst, this provides some limited improvement of colour maintenance over time, it is not sufficient to mitigate all of the current deficiencies observed by the consumer. Thus, in summary, none of the above currently described solutions to improve the colour maintenance over the time period in between colouring events are entirely satisfactory and there thus still exists a need to improve the colour maintenance in-between colouring events.

It has now been surprisingly found that application routines whereby a specific durable silicone conditioner treatment composition is applied to the hair after oxidative colouration, prior to at least one subsequent application of a colour refresher, overcomes at least one of these drawbacks. In particular, the present invention delivers the required initial colour and shine which is furthermore maintained over a longer time period without the need for an additional oxidative colouring event.

Whilst not wishing to be bound by theory, it is believed that the application of durable silicone conditioner treatment enhances the colour fade profile by one or more mechanisms. Firstly, by enhancing the condition of the hair, less mechanical damage occurs to the individual fibers, thereby enhancing their integrity. This in turn slows down the diffusion process of dyes from within the hair, which will lead to the maintenance of the oxidative colour for a longer time period. Secondly, the durable silicone conditioner treatment is also believed to alter the surface properties of coloured hair, thereby restoring some level of hydrophobicity to the hair surface. Consequently the rate at which water can diffuse into the hair and remove the oxidative dyes is also reduced. Moreover, the subsequent application of a colour refresher in the period of days and weeks after the oxidative colouring event enables the preformed dyes within the colour refresher to be taken onto the hair, further compensating for any loss in colour intensity or tone. In addition the restoration of the hydrophobicity of the hair along the entire hair shaft from root to tip allows for the more even uptake of the colour refresher preformed dyes. Furthermore due to the presence of the silicone conditioner treatment on the surface of the hair shaft which improves the cuticle condition, the wash fastness profile of the colour refresher preformed dyes is also improved. Finally the repeated application of the durable silicone conditioner with the colour refresher preformed dyes will further enhance these benefits.

SUMMARY OF THE INVENTION

The present invention relates to a hair colouring kit comprising i) a first individually packaged oxidising component comprising at least one oxidising agent, ii) a second individually packaged colourant component comprising at least one oxidative dye or at least one alkalizing agent or mixtures thereof, iii) a third individually packaged conditioner component comprising a functionalized silicone polymer having an interfacial tension (IFT) of from 1 to 12 mN/m and a viscosity of from 400 to 150,000 cps, wherein said silicone deposits durably on to hair, and iv) a fourth individually packaged colour refresher component comprising at least one preformed dye, water soluble or water dispersible dye.

The present invention further relates to a method of sequential hair colouring comprising the steps of at least two sequential hair colour treatments, wherein the time period between each treatment is from 1 minute to 60 days, more preferably from 1 day to 31 days, wherein said first colouring treatment comprises the steps of:
i) providing said first individually packaged oxidising component, said second individually packaged colourant component and said third individually packaged conditioner component as described herein,
ii) applying a mixture of said first and second individually packaged components to the hair and retaining said component composition on the hair for a period of from 2 minutes to 60 minutes, and subsequently rinsing said composition from the hair,
iii) subsequently applying said third conditioner component to the hair and retaining said component composition on the hair for a time period of from 5 seconds to 15 minutes and optionally subsequently rinsing said composition from the hair, and wherein said second coloring treatment comprises the steps of:
i) providing said individually packaged colour refresher component according to claim 1,
ii) applying said colour refresher component to the hair and retaining said component composition on the hair for a time period of at least 3 seconds to 30 minutes and then optionally rinsing said composition from the hair.

The present invention further includes embodiments comprising a hair colouring kit comprising: i) an individually packaged colour refresher composition comprising at least one performed or water soluble or water dispersible dye and ii) an individually packaged conditioner composition comprising a functionalized amino silicone having an interfacial tension (IFT) of from 1 to 12 mN/m and a viscosity of from 400 to 150000 cps, wherein said silicone despots durably on hair.

The present invention also includes hair colouring composition embodiments comprising i) a colour refresher component comprising at least one preformed or water soluble or water dispersible dye and ii) a conditioning agent comprising a functionalized amino silicone according to the formula:

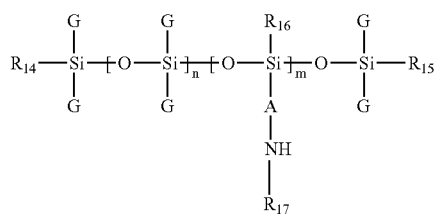

wherein, m and n are numbers with a sum (n+m) ranging from 2 to 2000, n is a number ranging from 1 to 1999, and m is a number ranging from 1 to 1999; and wherein m and n are selected such that ratio of m:n is from 1:1000 to 1:10, R14, R15, R16, which may be identical or different, are selected from a hydroxyl radical, C1-C4 alkoxy radicals and methyl radicals,
A is selected from linear and branched C3-C8 alkenyl radicals,
R17 is selected from H, phenyl, linear or branched C1-C4 alkyl radical, benzyl or linear or branched (C2-C8)NH2 groups,
G is selected from H, phenyl, hydroxyl, C1-C8 alkyl, preferably methyl, and wherein said aminosilicones is the random type or block type.

The present invention further relates to a method of sequential hair colouring comprising the steps of at least 2 sequential hair colouring treatments wherein the time period between each treatment is less than 14 days, wherein said first treatment comprises the steps of:
i) providing a first individually packaged oxidising component comprising at least one oxidising agent, a second individually packaged colourant component comprising at least one oxidative dye or at least one alkalising agent or mixtures thereof and a third individually packaged conditioner component comprising a conditioning agent
ii) applying a mixture of said first and second individually packaged components to the hair and retaining said composition on the hair for a period of from 2 to 60 minutes, and subsequently rinsing said composition from the hair and
iii) subsequently applying said third conditioner component to the hair and retaining said composition on the hair for a time period of from 5 seconds to 10 minutes and subsequently rinsing said composition from the hair, and wherein said second treatment comprises the steps of:
i) providing said individually packaged colour refresher component comprising at least one preformed or water soluble or water dispersible dye,
ii) applying said colour refresher component to the hair and retaining said composition on the hair for a time period of less than 10 minutes ad then rinsing said composition from the hair.

The present application further includes embodiments to the use of a hair colouring kit or hair colouring compositions described hereinabove to provide colour refreshment to coloured hair.

DETAILED DESCRIPTION OF THE INVENTION

Except as otherwise noted, amounts represent approximate weight percent of the actual amount of the ingredient, and do not include solvents, fillers or other materials which may be combined with the ingredient in commercially available products, and the amounts include the composition in the form of intended use. Except as otherwise noted, all amounts including part, percentages, and proportions are understood to be modified by the word "about", and amounts are not intended to indicate significant digits. All amounts are based on the final composition applied to the hair unless otherwise stated.

As used herein, the term "hair" refers to keratinous fibres on a living, e.g. a person, or non-living body, e.g. in a wig, hairpiece, or other aggregation of non-living keratinous fibres. Mammalian, preferably human, hair is preferred. Notably, hair, wool, fur, and other keratinous fibres are suitable substrates for colouring by the compounds and compositions described herein.

According to one embodiment of the present invention the hair colouring kits comprise a number of separate components: namely i) a first individually packaged oxidising component comprising at least one oxidising agent, ii) a second individually packaged colourant component comprising at least one oxidative dye or at least one alkalising agent or mixtures thereof, iii) a third individually packaged conditioner component comprising a functionalised silicone polymer as defined herein and iv) a fourth individually packaged colour refresher composition comprising at least one preformed dye.

Oxidizing Component

The oxidizing component compositions according to the present invention comprise at least one source of an oxidizing agent. Preferred oxidizing agents for use herein are water-soluble peroxygen oxidizing agents. "Water-soluble" as defined herein means that in standard condition at least 0.1 g, preferably 1 g, more preferably 10 g of said oxidizing agent can be dissolved in 1 liter of deionized water. The oxidizing agents are valuable for the initial solubilisation and decolourisation of the melanin (bleaching) and accelerate the oxidation of the oxidative dye precursors (oxidative dyeing) in the hair shaft.

Any oxidizing agent known in the art may be utilized in the present invention. Preferred water-soluble oxidizing agents are inorganic peroxygen materials capable of yielding hydrogen peroxide in an aqueous solution. Water-soluble peroxygen oxidizing agents are well known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts may be incorporated as monohydrates, tetrahydrates etc. Alkyl and aryl peroxides, and or peroxidases may also be used. Mixtures of two or more such oxidizing agents can also be used if desired. The oxidizing agents may be provided in aqueous solution or as a powder which is dissolved prior to use. Preferred for use in the compositions according to the present invention are hydrogen peroxide, percarbonate, persulphates and combinations thereof.

According to the present invention the compositions comprise from about 0.1% to about 15% by weight, preferably from about 1% to about 10% by weight, and most preferably from about 2% to about 7% by weight of an oxidizing agent.

Another preferred oxidizing agent for use herein is a source of peroxymonocarbonate ions. Preferably such a source is formed in situ from a source of hydrogen peroxide and a hydrogen carbonate ion source. Such an oxidizing agent has been found to be particularly effective at a pH of up to and including 9.5, preferably 7.5 to 9.5 more preferably about pH 9. Moreover, this system is also particularly effective in combination with a source of ammonia or ammonium ions. It has been found that this oxidizing agent can deliver improvements to the desired hair colour results particularly with regard to the delivery of high lift, whilst considerably reducing the odour, skin and scalp irritation and damage to the hair fibres.

Accordingly, any source of these ions may be utilized. Suitable sources for use herein include sodium, potassium, guanidine, arginine, lithium, calcium, magnesium, barium, ammonium salts of carbonate, carbamate and hydrocarbonate ions and mixtures thereof such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Percarbonate salts may also be utilized to provide both the source of carbonate ions and oxidizing agent. Preferred sources of carbonate ions, carbamate and hydrocarbonate ions are sodium hydrogen carbonate, potassium hydrogen carbonate, ammonium carbamate, and mixtures thereof.

According to the present invention the compositions comprise from about 0.1% to about 15% by weight, preferably from about 1% to about 10% by weight, and most preferably from about 1% to about 8% by weight of a hydrogencarbonate ion and from about 0.1% to about 10% by weight, preferably from about 1% to about 7% by weight, and most preferably from about 2% to about 5% by weight of a source of hydrogen peroxide.

Colourant Component

The compositions of the present invention comprise an oxidative hair colouring component composition which comprises at least one oxidative dye or at least one alkalizing agent or mixtures thereof. Such composition may be used to colour or bleach the whole head of hair or sections thereof to produce desired effects such as highlights. Such compositions may comprise oxidative hair dye precursors (also known as primary intermediates) that will deliver a variety of hair colours to the hair. These small molecules are activated by the oxidizing agent and react with further molecules to form a larger coloured complex in the hair shaft.

The precursors can be used alone or in combination with other precursors, and one or more can be used in combination with one or more couplers. Couplers (also known as colour modifiers or secondary intermediates) are generally colourless molecules that can form colours in the presence of activated precursors, and are used with other precursors or couplers to generate specific colour effects or to stabilize the colour. The choice of precursors and couplers will be determined by the colour, shade and intensity of colouration that is desired. The precursors and couplers can be used herein, singly or in combination, to provide dyes having a variety of shades ranging from ash blonde to black.

These compounds are well known in the art, and include aromatic diamines, aminophenols, aromaticdiols and their derivatives (a representative but not exhaustive list of oxidation dye precursor can be found in Sagarin, "Cosmetic Science and Technology", "Interscience, Special Edn. Vol. 2 pages 308 to 310). It is to be understood that the precursors detailed below are only by way of example and are not intended to limit the compositions and processes herein. These are: 1,7-Dihydroxynaphthalene (1,7-NAPHTHA-LENEDIOL), 1,3-Diaminobenzene(m-PHENYLENEDI-AMINE), 1-Methyl-2,5-diaminobenzene(TOLUENE-2,5-DIAMINE), 1,4-Diaminobenzene(p-PHENYLENEDIAMINE), 1,3-Dihydroxybenzene (RESORCINOL), 1,3-Dihydroxy-4-chlorobenzene, (4-CHLORORESORCINOL), 1-Hydroxy-2-aminobenzene, (o-AMINOPHENOL), 1-Hydroxy-3-aminobenzene(m-AMINOPHENOL), 1-Hydroxy-4-amino-benzene(p-AMINOPHENOL), 1-Hydroxynaphthalene(1-NAPHTHOL), 1,5-Dihydroxynaphthalene(1,5-NAPHTHALENEDIOL), 2,7-dihydroxynaphthalene(2,7-NAPHTHELENEDIOL)1-Hydroxy-2,4-diaminobenzene(4-DIAMINOPHENOL), 1,4-Dihydroxybenzene(HYDROQUINONE), 1-Hydroxy-4-methylaminobenzene(p-METHYLAMINOPHENOL), 6-Hydroxybenzo-morpholine(HYDROXYBENZOMORPHOLINE), 1-Methyl-2-hydroxy-4-aminobenzene(4-AMINO-2-HYDROXY-TOLUENE), 3,4-Diaminobenzoic acid(3,4-DIAMINOBENZOIC ACID), 1-Methyl-2-hydroxy-4-(2'-hydroxyethyl)aminobenzene(2-METHYL-5-HYDROXY-ETHYLAMINO-PHENOL), 1,2,4-Trihydroxybenzene(1,2,4-TRIHYDROXYBENZENE), 1-Phenol-3-methylpyrazol-5-on(PHENYLMETHYLPYRAZOLONE), 1-(2'-Hydroxyethyloxy)-2,4-diaminobenzene(2,4-DIAMI- NOPHENOXY-ETHANOL HCl), 1-Hydroxy-3-amino-2,4-dichlorobenzene(3-AMINO-2,4-DICHLORO-PHENOL), 1,3-Dihydroxy-2-methylbenzene(2-METHYLRESORCINOL), 1-Amino-4-bis-(2'-hydroxyethyl)aminobenzene(N,N-BIS(2-HYDROXY-ETHYL)-p-PHENYLENE-DIAMINE), 2,4,5,6-Tetraaminopyrimidine(HC Red 16), 1-Hydroxy-3-methyl-4-aminobenzene(4-AMINO-m-CRESOL), 2-methyl-5-hydroxyethylaminophenol, 1-Hydroxy-2-amino-5-methylbenzene(6-AMINO-m-CRESOL), 1,3-Bis-(2,4-Diaminophenoxy)propane(1,3-BIS-(2,4-DIAMINO-PHENOXY)-PROPANE), 1-(2'-Hydroxyethyl)-2,5-diaminobenzene (HYDROXYETHYL-p-PHENYLENE DIAMINE SULPHATE), 1-Methoxy-2-amino-4-(2'-hydroxyethylamino)benzene, (2-AMINO-4-HYDROXY-ETHYLAMINOANISOLE) 1-Hydroxy-2-methyl-5-amino-6-chlorobenzene(5-AMINO-6-CHLORO-o-CRESOL), 1-Hydroxy-2-amino-6-methylbenzene(6-AMINO-o-CRESOL), 1-(2'-Hydroxyethyl)-amino-3,4-methylenedioxybenzene(HYDROXYETHYL-3,4-METHYLENE-DIOXY-ANILINE HCl), 2,6-Dihydroxy-3,4-dimethylpyridine(2,6-DIHYDROXY-3,4-DIMETHYLPYRIDINE), 3,5-Diamino-2,6-dimethoxypyridine(2,6-DIMETHOXY-3,5-PYRIDINEDIAMINE), 5,6-Dihydroxyindole (DIHYDROXY-INDOLE), 4-Amino-2-aminomethylphenol (2-AMINOETHYL-p-AMINO-PHENOL HCl), 2,4-Diamino-5-methylphenetol(2,4-DIAMINO-5-METHYL-PHENETOLE HCl), 2,4-Diamino-5-(2'-hydroxyethyloxy)toluene(2,4-DIAMINO-5-METHYLPHENOXYETHANOL HCl), 5-Amino-4-chloro-2-methylphenol(5-AMINO-4-CHLORO-o-CRESOL), 4-Amino-1-hydroxy-2-(2'-hydroxyethylaminomethyl)benzene HYDROXYETHYLAMINOMETHYL-p-AMINO PHENOL HCl), 4-Amino-1-hydroxy-2-methoxymethylbenzene(2-METHOXYMETHYL-p-AMINOPHENOL HCl), 1,3-Bis(N(2-Hydroxyethyl)N(4-amino-phenyl)amino)-2-propanol(HYDROXYPROPYL-BIS-(N-HYDROXY-ETHYL-p-PHENYLENEDIAMINE)HCL), 6-Hydorxyindole(6-HYDROXY-INDOLE), 2,3-Indolinedione(ISATIN), 3-Amino-2-methylamino-6-methoxypyridine(HC BLUE NO. 7), 1-Phenyl-3-methyl-5-pyrazolone-2,4-dihydro-5,2-phenyl-3H-pyrazole-3-one, 2-Amino-3-hydroxypyridine(2-AMINO-3-HYDROXYPYRIDINE), 5-Amino-salicylic acid, 1-Methyl-2,6-bis(2-hydroxy-ethylamino)benzene(2,6-HYDROXYETHYLAMINO-TOLUENE), 4-Hydroxy-2,5,6-triaminopyrimidine(2,5,6-TRIAMINO-4-PYRIMIDI-NOL SULPHATE), 2,2'-[1,2-Ethanediyl-bis-(oxy-2,1-ethanediyloxy)]-bis-benzene-1,4-diamine(PEG-3,2',2'-DI-p-PHENYLENEDIAMINE), 5,6-Dihydroxyindoline (DIHYDROXYINDOLINE), N,N-Dimethyl-3-ureidoaniline(m-DIMETHYL-AMINO-PHENYLUREA), 2,4-Diamino-5-fluortoluenesulfatehydrate(4-FLUORO-6-METHYL-m-PHENYLENEDIAMINE SULPHATE) and 1-Acetoxy-2-methylnaphthalene(1-HYDROXYYETHYL-4,5-DIAMINOPYRAZOLE SULPHATE), 2,6-diaminopyridine. These can be used in the molecular form or in the form of peroxide-compatible salts.

The oxidative hair colouring component compositions of the present invention may also include non oxidative hair dyes, i.e. preformed or direct dyes which may be used alone or in combination with the above described oxidative dyes. Suitable direct dyes include azo or anthraquinone dyes and nitro derivatives of the benzene series and or melanin precursors and mixtures thereof. Such direct dyes are particularly useful to deliver shade modification or highlights. Particularly preferred are Basic Red 51, Basic Orange 31, Basic Yellow 87 and mixtures thereof.

The oxidative hair dye compositions of the present invention will generally comprise from about 0.001% to about 10% of dyes. For example compositions providing low intensity dyeing such as natural blonde to light brown hair shades generally comprise from about 0.001% to about 5%, preferably from about 0.1% to about 2%, more preferably from about 0.2% to about 1% by weight of dyeing composition of precursors and couplers. Darker shades such as browns and black typically comprise from 0.001% to about 10% by weight, preferably from about 0.05% to about 7% by weight, more preferably form about 1% to about 5% of precursors and couplers.

According to the present invention the colourant components may comprise at least one source of alkalizing agent, preferably a source of ammonium ions and or ammonia. Any agent known in the art may be used such as alkanolamides for example monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol and guanidium salts. Particularly, preferred alkalizing agents are those which provide a source of ammonium ions. Any source of ammonium ions is suitable for use herein. Preferred sources include ammonium chloride, ammonium sulphate, ammonium nitrate, ammonium phosphate, ammonium acetate, ammonium carbonate, ammonium hydrogen carbonate, ammonium carbamate, ammonium hydroxide, percarbonate salts, ammonia and mixtures thereof. Particularly preferred are ammonium carbonate, ammonium carbamate, ammonium hydrogen carbonate, ammonia and mixtures thereof. The compositions of the present invention may comprise from about 0.1% to about 10% by weight, preferably from about 0.5% to about 5%, most preferably from about 1% to about 3% of an alkalizing agent, preferably ammonium ions.

Conditioner Component

The compositions of the present invention further comprise a third conditioning component, wherein said component comprises at least one conditioner comprising a functionalised silicone polymer. Suitable silicones for use herein are characterised by specific physical properties. The functionalised silicone polymers suitable for use herein accordingly have an interfacial tension of 1 to 12 mN/m, preferably from 1 to 10 mN/m, more preferably 1 to 8 mN/m, most preferably from 1 to 4 mN/m. The functionalised silicone polymers for use herein have a viscosity in the range 400 to 150,000 mPa·s. More advantageously, the viscosity is in the range 600 to 100,000 mPa·s. More advantageously still, the viscosity is in the range 4000 to 25,000 mPa·s.

Surprisingly, it has been determined that the benefits associated with functionalized silicones having an interfacial tension and viscosity in the defined ranges apply regardless of chemistry, i.e., regardless of the functional groups concerned.

Functionalized silicone polymers which may be incorporated into compositions according to the invention include organomodified silicones of the pendant, graft or block type wherein these polar functional substituents for use in the present invention as described include, but are not limited to, polyoxyalkylene(polyether), primary and secondary amine, amide, quaternary ammonium, carboxyl, sulfonate, sulfate, carbohydrate, phosphate, and hydroxyl.

More preferably the functional silicones of the present invention include, but are not limited to silicones of the following structure:

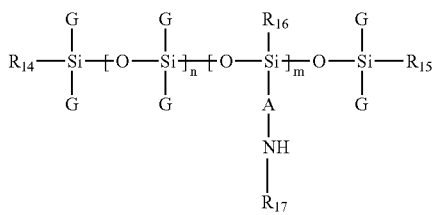

wherein m and n are numbers with a sum (n+m) ranging from 2 to 2000, n is a number ranging from 1 to 1999, and m is a number ranging from 1 to 1999; and are selected such that ratio of m:n is 1:1000 to 1:10, preferably 1:1000 to 1:25, more preferably 1:800 to 1:50, most preferably 1:500 to 1:50 and the sum m+n is in the range of from 150 to 2000, more preferably 250 to 1200, most preferably 300 to 800.

R14, R15, R16, which may be identical or different, which are selected from a hydroxyl radical, C1-C4 alkoxy radicals and methyl radicals. A is selected from linear and branched C3-C8 alkyl radicals. R17 is selected from H, phenyl, linear or branched C1-C4 alkyl radical, benzyl or linear or branched (C2-C8)NH2 groups. G is selected from H, phenyl, hydroxyl, C1-C8 alkyl, preferably methyl. The aminosilicones may be of the random type or block type.

Polymers which are then subsequently reacted with a carbinol compound, preferably glycidol, are also included in the description.

Suitable functionalized silicones of the present invention include, but are not limited to, organomodified silicones with amine functionality available commercially under the trade names such as ADM100 and ADM1600 from Wacker Silicones, DC2-8211, DC8822, DC8822A, DC8803, DC2-8040, DC2-8813, DC2-8630 and DC8566 from Dow Corning Corporation, KF-862, KF-861, KF-862S, KF-8005, KF-8004, KF-867S, KF-873, and X-52-2328 from Shin-Etsu Corporation, and TSF 4702, TSF 4703, TSF 4704, TSF 4705, TSF 4707, TSF 4708, TSF 4709, F42-B3115, SF 1708, SF 1923, SF 1921, SF 1925, OF TP AC3309, OF 7747, OF-NH TP A13631, OF-NH TP A13683 from GE Bayer Silicones.

Highly preferred functionalized silicones of the present invention are organomodified silicones with amine functionality with viscosities of greater than 4,000 mPa·s which include, but are not limited to, commercially available fluids under the trade names ADM1100 from Wacker Silicones, DC8803 from Dow Corning Corporation, and TSF 4707 from GE Bayer Silicones.

The functionalized silicones herein can be used together with a durability additive. The durability additive is capable of modifying the functionalized silicones to render them more durable on polar fibrous substrates, especially where the substrate is hair that has been previously damaged through chemical treatments, such as occurs during permanent dyeing, bleaching and permanent waving. The durability additive must be miscible with the functionalized silicone wherein the mixture has a (Tan $\delta$)$^{-1}$ greater than zero, and: Tan $\delta$=G"/G', where G' is the storage modulus and G" is the loss modulus. Tan $\delta$ describes the ratio of energy lost to energy stored, where Tan $\delta$=G"/G', G" is the loss modulus and G' is the storage modulus. More information on the measurement of dynamic rheological properties can be found in "Rheological Properties of Cosmetics and Toiletries" by Dennis Laba, Cosmetic Science and Technology Series, Volume 13, Marcel Dekker, Inc., ISBN 0-8247-9090-1 referred to heirein by reference. For the avoidance of doubt, (Tan $\delta$)$^{-1}$ is directly equivalent to 1/(Tan $\delta$).

Preferably, the durability additive according to the invention comprises one or more organosiloxane resins. Without wishing to be bound by theory, organosiloxane resins are believed to create a 3-dimensional network within the functionalized silicone fluid giving rise to vicoelasticity thereby improving the adhesive properties of the fluid and hence the durability on a fibrous substrate. Preferably, the organosiloxane resin is insoluble in water.

More preferably, the organosiloxane resins comprise repeating monofunctional $R_3SiO_{1/2}$ "M" units and the quadrafunctional $SiO_2$ "Q" units, otherwise known as "MQ" resins. In this case, the ratio of the "M" to "Q" functional units is advantageously from 0.7 and the value of n is 1.2. Organosiloxane resins such as these are commercially available as SR1000 available from GE Bayer Silicones and Wacker 803 from Wacker Silicones.

Advantageously, the organosiloxane resins according to the invention are solid at about 25° C. and have a molecular weight range of from 1,000 to 10,000 grams/mole.

The conditioning composition according to the present invention may include a cosmetically acceptable vehicle to act as a diluent, dispersant, or carrier for the silicone oil in the composition, so as to facilitate the distribution of the silicone oil when the composition is applied. The vehicle may be an aqueous emulsion, water, liquid or solid emollients, solvents, humectants, propellants, thickeners and powders.

Advantageously, the conditioning compositions according to the present invention may be in the form of an emulsion with water as a primary component, although aqueous organic solvents, such as those listed above, may also be included. The emulsion may be a water-in-oil emulsion, an oil-in-water emulsion, a water-in-oil-in-water multiple emulsion, or an oil-in-water-in-oil multiple emulsion, but is preferably an oil-in-water emulsion (a silicone-in-water emulsion). In such a case the functionalized silicone particle size is preferably greater than 500 nm, more preferably greater than 1 μm and even more preferably greater than 2 μm.

The aqueous continuous phase of the emulsion may further comprise an emulsifier to facilitate the formation of the emulsion. Emulsifiers for use in the aqueous continuous phase of the emulsion may include an anionic surfactant, cationic surfactant, amphoteric surfactant, water-soluble polymeric surfactant, water-soluble silicone-containing surfactant, nonionic surfactant having an HLB of greater than about 10, or a surfactant system capable of forming stabilizing liquid crystals around the silicone droplets. The nonionic surfactant preferably has an HLB of at least 12, and more preferably, an HLB value of at least about 15. Surfactants belonging to these classes are listed in McCutcheon's Emulsifiers and Detergents, North American and International Editions, MC Publishing Co., Glen Rock N.J., pages 235-246 (1993).

The emulsifier for the aqueous phase does not gel the aqueous phase. The emulsifier however may be capable of forming a stabilizing layer of lamellar liquid crystals around silicone droplets. For conciseness, the term "liquid crystal structure" as used herein, should be taken to also include gel networks, which are solidified liquid crystals. The surfactant system can be a single surfactant or a blend of surfactants. In some cases, a particular surfactant cannot form a liquid crystal structure alone, but can participate in the formation of liquid crystals in the presence of a second surfactant.

Exemplary classes of surfactants capable of participating in the formation of a liquid crystal, include but are not limited to specific cationic surfactants, anionic surfactants, nonionic surfactants, quaternary ammonium surfactants and lipid surfactants.

The conditioning component compositions according to an embodiment of the invention may be provided at a pH from about 3 to 11, preferably from about 4 to 10.5.

The conditioning compositions according to the present invention may be provided in any suitable physical form, for example as low to moderate to high viscosity liquids, lotions, milks, mousses, dispersions, sprays, gels, foams, aerosols, and creams. These compositions may be produced by procedures well known to the skilled artisan. The conditioning component compositions of the present invention can be formulated as a fluid, lotion, fluid cream or cream having a viscosity of from 500 to 100,000 mPa·s or above. The conditioner component comprises from 0.1% to 20%, preferably from 0.2% to 10%, more preferably from 0.5% to 7.5% by weight of said functionalized silicone.

Colour Refresher Component

According to the present invention the colour refersher component comprises at least one preformed dye precursor or water soluble or water dispersible dye or mixtures thereof. These compounds are known in the art and include acid dyes, basic dyes, disperse dyes, reactive dyes and mixtures thereof. A representative but not exhaustive list can be found in (i) Colour Index 3rd Ed; Society of Dyers & Colourists: Bradford, West Yorkshire & the American Association of Textile Chemists & Colourists: Research Triangle Park 1971 and (ii) International Cosmetic Ingredient Dictionary and Handbook, 10th ed. (2004). Suitable dyes for use herein include:

For example for acid dyes: Acid Red 27 (C.I. 16185), Acid Red 51 (C.I. 45430), Acid Red 18 (C.I. 16255), Acid Red 92 (C.I. 45410), Acid Red 94 (C.I. 45440), Acid Red 52 (C.I. 45100), Acid Yellow 23 (C.I. 19140), Food Yellow 3 (C.I. 15985), Food Green 3 (C.I. 42053), Food Blue 2 (C.I. 42090), Acid Blue 74 (C.I. 73015), Pigment Red 57-1 (C.I. 15850), Acid Red 33 (C.I. 17200), Acid Red 87 (C.I. 45380), Acid Orange 7 (C.I. 15510), Acid Red 95 (C.I. 45425), Acid Yellow 73 (C.I. 45350), Acid Yellow 3 (C.I. 47005), Acid Green 25 (C.I. 61570), Solvent Green 7 (C.I. 59040), Solvent Violet 13, Acid Green 5 (C.I. 42095), Acid Blue 5 (C.I. 42052), Acid Blue 9 (C.I. 42090), Acid Orange 24 (C.I. 20170), Acid Violet 9 (C.I. 45190), Food Red 6 (C.I. 16155), Acid Red 26 (C.I. 16150), Food Red 1 (C.I. 14700), Acid Red 88 (C.I. 15620), Acid Orange 20 (C.I. 14600), Acid Yellow 40 (C.I. 18950), Acid Yellow 1 (C.I. 10316), Acid Yellow 36 (C.I. 13065), Acid Yellow 11 (C.I. 18820), Acid Green 1 (C.I. 10020), Acid Green 3 (C.I. 42085), Acid Violet 43 (C.I. 60730), Acid Black 1 (C.I. 20470), Acid Black 52 (C.I. 15711), Acid Blue 1 (C.I. 42045), Acid Blue 3 (C.I. 42051), Acid Blue 62 (C.I. 62045), Acid Brown 13 (C.I. 10410), Acid Green 50 (C.I. 44090), Acid Orange 3 (C.I. 10385), Acid Orange 6 (C.I. 14270), Acid Red 14 (C.I. 14720), Acid Red 35 (C.I. 18065), Acid Red 73 (C.I. 27290), Acid Red 184 (C.I. 15685), and Brilliant Black 1 (C.I. 28440).

Examples of the basic dyes include Basic Blue 7 (C.I. 42595), Basic Blue 16 (C.I. 12210), Basic Blue 22 (C.I. 61512), Basic Blue 26 (C.I. 44045), Basic Blue 99 (C.I. 56059), Basic Blue 117, Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 12 (C.I. 48070), Basic Red 22 (C.I. 11055), Basic Red 51, Basic Red 76 (C.I. 12245), Basic Red 118 (C.I. 12251:1), Basic Orange 31, Basic Orange 69, Basic Yellow 28 (C.I. 48054), Basic Yellow 57 (C.I. 12719), Basic Yellow 87, and Basic Black 2 (C.I. 11825); basic dyes containing a quaternary nitrogen atom in the side chain of an aromatic ring skeleton, the dyes disclosed in, for example, Japanese Patent Publication (kokoku) No. 58-2204 and Japanese Patent Application Laid-Open (kokai) No. 9-118832; and basic dyes disclosed in, for example, Japanese Kohyo Patent Publication No. 10-502946 and Japanese Patent Application Laid-Open (kokai) Nos. 10-182379 and 11-349457.

Examples of the preformed dyes other than acid dyes and basic dyes include 2-amino-3-nitrophenol, 2-amino-4-nitrophenol, 2-amino-5-nitrophenol, 4-amino-3-nitrophenol, 2-amino-6-chloro-4-nitrophenol, 4-hydroxypropylamino-3-nitrophenol, 3-nitro-p-hydroxyethylaminophenol, 2-nitro-p-phenylenediamine, 4-nitro-o-phenylenediamine, 4-nitro-m-phenylenediamine, 6-nitro-o-toluidine, 6-nitro-p-toluidine, hydroxyethyl-2-nitro-p-toluidine, N,N'-bis(2-hydroxyethyl)-2-nitro-p-phenylenediamine, 2-chloro-5-nitro-N-hydroxyethyl-p-phenylenediamine, 2-nitro-5-glycerylmethylaniline, 4-amino-2-nitrophenylamine-2-carboxylic acid, 2-chloro-6-ethylamino-4-nitrophenol, 3-methylamino-4-nitrophenoxyethanol, N-ethyl-3-nitro-PABA, picramic acid, 2-hydroxyethylpicramic acid, 4-nitrophenylaminoethylurea, Solvent Violet 13 (C.I. 60725), Solvent Yellow 44 (C.I. 56200), Disperse Red 17 (C.I. 11210), Disperse Violet 1 (C.I. 61100), Disperse Violet 4 (C.I. 61105), Disperse Black 9, Disperse Blue 377, Disperse Blue 23, Disperse Blue 3 (C.I. 61505), Disperse Blue 7 (C.I. 62500), HC Violet No. 1, HC Green No. 1, HC Blue No. 2, HC Blue No. 7, HC Blue No. 8, HC Blue No. 9, HC Blue No. 10, HC Blue No. 12, HC Blue No. 14, HC Orange No. 1, HC Orange No. 2, HC Orange No. 3, HC Red No. 1, HC Red No. 3, HC Red No. 7, HC Red No. 8, HC Red No. 9, HC Red No. 10, HC Red No. 11, HC Red No. 13, HC Red No. 14, HC Red No. 16, HC Violet No. 2, HC Yellow No. 2, HC Yellow No. 4, HC Yellow No. 5, HC Yellow No. 6, HC Yellow No. 7, HC Yellow No. 9, HC Yellow No. 10, HC Yellow No. 11, HC Yellow No. 12, HC Yellow No. 13, HC Yellow No. 14 and HC Yellow No. 15.

Preferred preformed dyes for use herein may be selected from Acid Black 1, Acid Orange 3, Acid Red 18, Acid Red 92, Acid Violet 43, Acid Yellow 1, Basic Red 51, Basic Orange 31, Basic Yellow 57, Basic Yellow 87, Basic Blue 7, Basic Blue 99, Basic Brown 16, Basic Red 76, Basic Yellow 57, Basic Brown 17, Basic Brown 16, Basic red 118, Basic Orange 69, Basic Violet 2, Curry Red, D&C Green 3, D&C Green 5, D&C Green 6, D&C Orange 4, D&C Red 33, D&C Yellow 10, Disperse Blue 3, Disperse Blue 3 (solvent form), Disperse Blue 377, Disperse black 9, Disperse Red 17, Disperse Violet 1, FD&C Blue 1, FD&C Red 4, FD&C Red 30 lake, FD&C Yellow 5, FD&C Yellow 5 Zr Lake, FD&C Yellow 6, ex. FD&C Yellow 7, HC Blue 12, HC Blue 15, HC Orange 1, HC Red 1, HC Red 3, HC Red 10 & 11, HC Red 13, HC Blue 2, HC Yellow 2, HC Yellow 4, HC Yellow 13, HC Yellow 6, Pigment Red 57, Solvent Violet 13, 4-amino-3-nitrophenol, 3-nitro-p-hydroxyethylaminophenol, 4-nitrophenylaminoethylurea, 2-amino-6-chloro-4-nitrophenol, 6-amino-m-cresol, 2-nitro-p-phenylenediamine, picramic acid, 2-hydroxyethylpicramic acid, hydroxyethyl-2-nitro-p-toluidine, 2-chloro-6-ethylamino-4-nitrophenol, 2-amino-6-chloro-4-nitrophenol, 4-hydroxypropylamino-3-nitrophenol, 2,6-diamino-3-((pyridine-3-yl)azo)pyridine, tetrabromophenol Blue and mixtures thereof.

In an alternative embodiment of the present invention the colour refresher component may comprise a combination of oxidative dyes and preformed dyes. Particularly preferable are combinations in the form of an aqueous or aqueous alcoholic solution comprising oxidative dye(s) and at least 3 preformed dyes whereby the weight ratio of oxidative dye to preformed dyes is 5:1 to 0.5:1. Preferred oxidative dyes are 2,5-diamino toluol, 2,4-diaminophenoxyethanol, resorcinol, 2-methylresorcinol, m-aminophenol, 4-amino-3-methylphenol, 4-amino-2-hydroxy-toluol, 6-amino-3-methyl phenol, 2-amino-4-hydroxyethylaminoanisol, 1-napthol, hydroxyethyl-3,4-methylenedioxyanilin, 2-5-diamino-phenoletha-nol, N,N-bis(2-hydroxyethyl)p-phenylenediamine, phenyl-methyl-pyrazolone, 1-hydroxyethyl-4,5-diaminopyrazol and 2-arnino-chloro-4-vitro-phenol or the salts thereof. Preferred preforemd dyes are selected from hydroxyethyl-2-nitro-ptoluidin, 2-hydroxyethyl-pikraminacid, 4-nitrophenyl-ami-nourea, basic violet 2, disperse violet 1, HC Blue No. 2, HC Blue No. 12, HC Red No. 13, HC Yellow No. 6, HC Red No. 3,4-amino-3-nitrophenol, 4-[(hydroxyethyl)(-anino]-3-nitrophenol, HC Red No. 10, HC red No. 11, 2-chloro-6-ethylamino-4-nitrophenol, 2-amino-6-chloro-4-nitrophenol, HC Yellow No. 13, Basic Blue no. 99, Basic Brown No. 16, Basic Brown No. 17, Basic Yellow No 57 and 2,6,diamino-3[(pyridine-3-yl)azo]-pyridine and the salts thereof.

The colour refresher component compositions of the present invention will typically comprise from about 0.01% to 10.0% preferably from about 0.01% to 3.0%, by weight of said preformed dyes.

The colour refresher can further optionally further comprise the functional silicone polymer as described hereinabove in the conditioner component.

Additional Components

Any of the component compositions of the present invention described hereinabove may further comprise additional ingredients which may include optional benefit materials and cosmetic adjuncts, as long as the benefit materials or the adjuncts do not eliminate or substantially reduce the performance or shelf stability of the composition. Suitable ingredients include but are not limited to, for example dyes and colouring agents; fragrances; anionic, cationic, non-ionic, amphoteric or zwitterionic surfactants; buffers, masking fragrances, dispersing agents, stabilizers, cationic polymers, perfumes, non-ionic polymers, anionic polymers, complex coacervates, complex coacervate capsules, metal salts, lewis acids, buffering agents, thickeners and or rheology modifiers, polymeric thickeners, wax thickeners, oils, emollients, humectants, moisturizers, pearlescents, opacifiers, enzymes, suspending agents, antimicrobials, preservatives, proteins, herb and plant extracts, bleach, peroxide, perming actives, polyols, silicones, antibodies, pH adjusting agents including pH buffers, alkalizing angets, preservatives, viscosity enhancers, gelling agents, chelators, oxidising agents, reducing agents, UV filters, emulsifying agents, antioxidants, moisturizing agents and conditioning agents, and hair dyeing agents such as oxidative dye precursors, non-oxidative preformed dyes and other common adjuvants well known to those skilled in the art. Some of these additional components are detailed hereafter.

Surfactants

The component compositions may further comprise surfactants. Anionic, cationic, non-ionic, zwitterionic surfactant (s) or mixtures thereof can be used herein. Preferred for use are anionic surfactants (at concentration in range 0.1-30%), non-ionic surfactant (range 0.1-20%) and zwitterionic surfactants (range 0.1-20%)

Conditioning Agents

The component compositions may also comprise a conditioning active chosen from, sunscreens, vitamins, provitamins such as panthenol, silicones, organofunctional silicones, proteins, protein hydrosylates, 18-methyleicosanoic acid, anionic, cationic, non-ionic, amphoteric or zwitterionic surfactants; complex coacervates, complex coacervate capsules, oils, emollients, humectants, moisturizers, herb and plant extracts, polyols, UV filters and conditioning agents, and other common adjuvants well known to those skilled in the art, and also mixtures of these various compounds and any other additive usually used in cosmetic compositions. These additives may be present in the composition in proportions that may range between 0 and 20% by weight relative to the total composition. The amount of each additive required can be determined by a person skilled in the art, depending on the composition's nature and its function.

Radical Scavenger

According to the present invention the component compositions may further comprise a source of radical scavenger. As used herein the term radical scavenger refers to a species that can react with a reactive radical, preferably carbonate radicals, to convert the reactive radical by a series of fast reactions to a less reactive species.

Suitable radical scavengers for use herein include compounds according to the general formula:

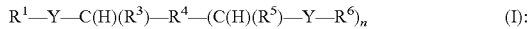

$$R^1\text{—}Y\text{—}C(H)(R^3)\text{—}R^4\text{—}(C(H)(R^5)\text{—}Y\text{—}R^6)_n \quad (I):$$

wherein Y is $NR^2$, O, or S, preferably $NR^2$, n is 0 to 2, and wherein $R^4$ is monovalent or divalent and is selected from: (a) substituted or unsubstituted, straight or branched, alkyl, mono- or poly-unsaturated alkyl, heteroalkyl, aliphatic, heteroaliphatic, or heteroolefinic systems, (b) substituted or unsubstituted, mono- or poly-cyclic aliphatic, aryl, or heterocyclic systems, or (c) substituted or unsubstituted, mono-, poly-, or per-fluoro alkyl systems; the systems of (a), (b) and (c) comprising from 1 to 12 carbon atoms and 0 to 5 heteroatoms selected from O, S, N, P, and Si; and wherein $R^4$ can be connected to $R^3$ or $R^5$ to create a 5, 6 or 7 membered ring; and wherein $R^1$, $R^2$, $R^3$, $R^5$, and $R^6$ are monovalent and are selected independently from: (a), (b) and (c) described herein above, or H.

Preferably, $R^4$ is selected from: (a) substituted or unsubstituted, straight or branched, alkyl, heteroalkyl, aliphatic, heteroaliphatic, or heteroolefinic systems, (b) substituted or unsubstituted, mono- or poly-cyclic aliphatic, aryl, or heterocyclic systems, or (c) substituted or unsubstituted, mono-, poly-, or per-fluoro alkyl systems; more preferably $R^4$ is selected from (a) substituted or unsubstituted, straight or branched, alkyl, heteroalkyl, aliphatic, or heteroaliphatic systems, (b) substituted or unsubstituted, aryl, or heterocyclic systems, or (c) substituted or unsubstituted, mono-, poly-, or per-fluoro alkyl systems; more preferably substituted or unsubstituted, straight or branched, alkyl, or heteroalkyl systems.

Preferably, the $R^4$ systems of (a), (b), and (c), described herein above, comprise from 1 to 8 carbon atoms, preferably from 1 to 6, more preferably from 1 to 4 carbon atoms and from 0 to 3 heteroatoms; preferably from 0 to 2 heteroatoms; most preferably from 0 to 1 heteroatoms. Where the systems contain heteroatoms, preferably they contain 1 heteroatom. Preferred heteroatoms include O, S, and N; more preferred are O, and N; and most preferred is O.

Preferably, $R^1$, $R^2$, $R^3$, $R^5$, and $R^6$ are selected independently from any of the systems defined for $R^4$ above, and H.

In alternative embodiments, any of $R^1$, $R^2$, $R^3$, $R^4$, $R^5$, and $R^6$ groups are substituted. Preferably, the substituent(s) is selected from: (a) the group of C-linked monovalent substituents consisting of: (i) substituted or unsubstituted, straight or branched, alkyl, mono- or poly-unsaturated alkyl, heteroalkyl, aliphatic, heteroaliphatic, or heteroolefinic systems, (ii) substituted or unsubstituted, mono- or poly-cyclic aliphatic, aryl, or heterocyclic systems, or (iii) substituted or unsubstituted, mono-, poly-, or per-fluoro alkyl systems; said systems of (i), (ii) and (iii) comprising from 1 to 10 carbon atoms and 0 to 5 heteroatoms selected from O, S, N, P, and Si; (b) the group of S-linked monovalent substituents consisting of $SA^1$, SCN, $SO_2A^1$, $SO_3A^1$, $SSA^1$, $SOA^1$, $SO_2NA^1A^2$, $SNA^1A^2$, and $SONA^1A^2$; (c) the group of O-linked monovalent substituents consisting of $OA^1$, OCN and $ONA^1A^2$; (d) the group of N-linked monovalent substituents consisting of $NA^1A^2$, $(NA^1A^2A^3)^+$, NC, $NA^1OA^2$, $NA^1SA^2$, NCO, NCS, $NO_2$, N=$NA^1$, N=$NOA^1$, $NA^1CN$, $NA^1NA^2A^3$; (e) the group of monovalent substituents consisting of $COOA^1$, $CON_3$, $CONA^1_2$, $CONA^1COA^2$, $C(=NA^1)NA^1A^2$, CHO, CHS, CN, NC, and X; and (f) the group consisting fluoroalkyl monovalent substituents consisting of mono-, poly-, or per-fluoro alkyl systems comprising from 1 to 12 carbon atoms and 0 to 4 heteroatoms.

For the groups (b) to (e), described above, $A^1$, $A^2$, and $A^3$ are monovalent and are independently selected from: (1) H, (2) substituted or unsubstituted, straight or branched, alkyl, mono- or poly-unsaturated alkyl, heteroalkyl, aliphatic, heteroaliphatic, or heteroolefinic systems, (3) substituted or unsubstituted, mono- or poly-cyclic aliphatic, aryl, or heterocyclic systems, or (4) substituted or unsubstituted, mono-, poly-, or per-fluoro alkyl systems; said systems of (2), (3) and (4) comprising from 1 to 10 carbon atoms and 0 to 5 heteroatoms selected from O, S, N, P, and Si; and wherein X is a halogen selected from the group consisting of F, Cl, Br, and I.

Preferred substituents for use herein include those having a Hammett Sigma Para ($\sigma_p$) Value from −0.65 to +0.75, preferably from −0.4 to +0.5. Hammett Sigma Values are described in Advanced Organic Chemistry—Reactions, Mechanisms and Structure (Jerry March, $5^{th}$ ed. (2001) at pages 368-375).

Alternative suitable radical scavengers for use herein are compounds according to the general formula (II):

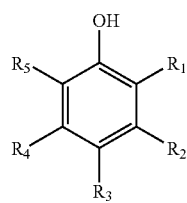

(II)

wherein $R_1$, $R_2$, $R_3$, $R_4$, and $R_5$ are each independently selected from H, $COO^-M^+$, Cl, Br, $SO_3^-M^+$, $NO_2$, $OCH_3$, OH or a $C^1$ to $C^{10}$ primary or secondary alkyl and M is either H or alkali metal. Preferably, the above-described radical scavengers have a pKa of more than 8.5 to ensure protonation of the hydroxy goup.

Other suitable radical scavengers for use herein include those selected from group (III) benzylamine, imidazole, di-tert-butylhydroxytoluene, hydroquinone, guanine, pyrazine, piperidine, morpholine, methylmorpholine, 2methoxyethylamine, and mixtures thereof.

Preferred radical scavengers according to the present invention are selected from the classes of alkanolamines, amino sugars, amino acids, esters of amino acids and mixtures thereof. Particularly preferred compounds are: monoethanolamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methyl-propan-2-ol, 3-aminopropane-1,2-diol, glucosamine, N-acetylglucosamine, glycine, arginine, lysine, proline, glutamine, histidine, sarcosine, serine, glutamic acid, tryptophan, and mixtures thereof, and the salts such as the potassium, sodium and ammonium salts thereof and mixtures thereof. Especially preferred compounds are glycine, sarcosine, lysine, serine, 2 methoxyethylamine, glucosamine, glutamic acid, morpholine, piperdine, ethylamine, 3 amino-1-propanol and mixtures thereof.

The radical scavengers according to the present invention preferably have a molecular weight of less than about 500, preferably less than about 300, more preferably less than about 250 in order to facilitate penetration of the radical scavenger into the hair fibre. The compositions of the present invention preferably comprise from about 0.1% to about 10% by weight, preferably from about 1% to about 7% by weight of radical scavenger. The radical scavenger is also preferably selected such that it is not an identical species as the alkalizing agent. According to one embodiment of the present invention the radical scavenger may be formed insitu in the hair dyeing compositions prior to application to the hair fibres.

Polymers

The component compositions of the present invention may optionally further comprise at least about 0.01% of polymer. The polymer can be chosen, for example, from associative polymers. As used herein, the expression "associative polymer" means an amphiphilic polymer comprising both hydrophilic units and hydrophobic units, for example, at least one C8-C30 fatty chain and at least one hydrophilic unit. Representative associative polymers that may be used are associative polymers chosen from:

(i) nonionic amphiphilic polymers comprising at least one fatty chain and at least one hydrophilic unit; for example celluloses or hydroxyethylcelluloses modified with groups comprising at least one fatty chain, hydroxypropyl guars modified with groups comprising at least one fatty chain, polyether urethanes comprising at least one fatty chain, copolymers of vinylpyrrolidone and of fatty-chain hydrophobic monomers, copolymers of C1-C6 alkyl acrylates or methacrylates and of amphiphilic monomers comprising at least one fatty chain, copolymers of hydrophilic acrylates or methacrylates and of hydrophobic monomers comprising at least one fatty chain.

(ii) anionic amphiphilic polymers comprising at least one hydrophilic unit and at least one fatty-chain unit; these, for example, may be chosen from those comprising at least one fatty-chain allyl ether unit and at least one hydrophilic unit comprising an ethylenic unsaturated anionic monomeric unit, or from those comprising at least one hydrophilic unit of unsaturated olefinic carboxylic acid type, and at least one hydrophobic unit of the type such as a (C8-C30) alkyl ester or oxylakylenated (C8-C30) alkyl ester of an unsaturated carboxylic acid; anionic amphopilic polymers may be further cross-linked.

(iii) cationic amphiphilic polymers comprising at least one hydrophilic unit and at least one fatty-chain unit; these, for example, may be chosen from quatemized cellulose derivatives and polyacrylates comprising amino side groups.

(iv) amphoteric amphiphilic polymers comprising at least one hydrophilic unit and at least one fatty-chain unit; mention may be made, for example, of methacrylamidopropyltrimethylammonium chloride/acrylic acid/C10-C30 alkyl methacrylate copolymers, wherein the alkyl radical is, for example, a stearyl radical.

Further, the polymer can be chosen from crosslinked acrylic acid homopolymers, crosslinked copolymers of (meth)acrylic acid and of (C1-C6)alkyl acrylate or polysaccharides.

The polymer may also serve as conditioning agents, as described herein. The polymer will generally be used at levels of from about 0.01% to about 20.0% by weight of the composition, preferably of from about 0.1% to about 5%.

Chelants

According to the present invention the component compositions may comprise chelants. Chelants are well known in the art and refer to a molecule or a mixture of different molecules each capable of forming a chelate with a metal ion. Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996) both incorporated herein by reference.

Examples of chelants suitable for use herein include EDDS (ethylenediaminedisuccinic acid), carboxylic acids (in particular aminocarboxylic acids), phosphonic acids (in particular aminophosphonic acids) and polyphosphoric acids (in particular linear polyphosphoric acids), their salts and derivatives.

Chelants may be incorporated into the composition of the present invention as stabilizers and or preservatives. In addition it has also been found that chelants provide hair fibre damage benefits and thus they may be utilized in order to further improve the hair damage profile of the present invention. Levels of chelants in the present invention may be as low as about 0.1%, preferably at least about about 0.25%, more preferably about 0.5% for the most effective chelants such as diamine-N,N'-dipolyacid and monoamine monoamide-N,N'-dipolyacid chelants (for example EDDS). Less effective chelants will be more preferably used at levels of at least about 1%, even more preferably above about 2% by weight of the composition, depending of the efficiency of the chelant. Levels as high as about 10% can be used, but above this level significant formulation issues may arise.

Solvents

Suitable solvents for use in the compositions of the present invention include, but are not limited to, water, butoxydiglycol, propylene glycol, alcohol (denat.), ethoxydiglycol, isopropylalcohol, hexylene glycol, benzyl alcohol and dipropylene glycol. Finally, the compositions according to the present invention are thus typically provided as an aqueous composition. The compositions of the present invention typically comprise from at least about 10%, preferably from about 20%, more preferably from about 30% and most preferably from about 50% by weight of solvent.

Method of Use

It is understood that the examples of methods of use and embodiments described herein are for illustrative purposes only and that various modifications or changes in light thereof will be suggested to one skilled in the art without departing from the scope of the present invention.

Oxidative hair dye compositions are usually sold in kits comprising, in individually packaged components such as separate containers, an oxidising component (also called "hydrogen peroxide cream" for emulsions or "hydrogen peroxide liquid" for solutions) comprising the oxidizing agent (usually hydrogen peroxide) and a colourant component (also called "dye cream" for emulsions or "dye liquid" for solutions) comprising the oxidative dye, precursors and or alkalizing agent which is typically ammonia in a suitable carrier. The consumer mixes the colourant component and the oxidising component together immediately before use and applies it onto the hair.

Similarly, bleaching compositions are also usually sold as a kit comprising two or three individually packaged components typically in two or three separate containers. The first component comprises the oxidising agent, the second component comprises the alkalizing agent such as an ammonium ion source (e.g. ammonia), and the third component comprises a second oxidizing agent. The bleaching compositions are obtained by mixing the above-mentioned compositions immediately before use.

After working the mixture for a few minutes (to insure uniform application to all of the hair), the oxidative dye composition is allowed to remain on the hair for an amount sufficient for the dyeing to take place (usually from about 2 to 60 minutes, typically about 30 to 45 minutes). The consumer then rinses his/her hair thoroughly with water and allows it to dry. It is observed that the hair has changed from its original colour to the desired colour.

The kits of the present invention also further comprise a conditioning component composition, provided in a third container. The oxidising component, colourant component and conditioner component can be mixed together immediately before use and applied together, or preferably the content of the third container can be applied (after an optional rinse step) as a post-treatment immediately after the oxidative dye composition or bleaching composition resulting from the mixture of the other containers.

The kit finally also comprises a colour refresher component composition comprising at least one preformed dye, or water soluble or water dispersible dye. The colour refresher typically further comprises surfactants and or conditioning agents to aid application of the composition on hair so that the colour refresher may be applied as a shampoo or conditioner step, whereby the composition is applied to the hair worked for a few minutes and then optionally rinsed off.

A further embodiment of the present invention relates to hair colouring kits comprising an individually packaged colour refresher component composition comprising at least one preformed dye or water soluble or water dispersible dye and an individually packaged conditioner component composition comprising a comprising a functionalised amino silicone. Such kits provide the hair colourant consumer with the ability to further top up and or maintain the original colour provided by an oxidative colouring system without applying an additional oxidative colouring step.

In a further embodiment of the present invention, a hair colouring composition is provided that comprises a colour refresher component comprising at least one preformed dye or water soluble or water dispersible dye and a conditioning agent comprising a functionalised amino silicone as defined hereinabove.

According to a particularly preferred embodiment, the colour refresher component of any of the embodiments described herein comprises a sufficient amount in order to apply at least 1 application, preferably at least 2 applications more preferably at least 4 applications of the colour refresher composition on the hair.

According to the present invention the individual components may be provided in a variety of forms such as liquids, gels, foams, mousses and sprays.

Device Disclosure

The present invention may be utilized in a variety of packaging and dispensing devices. These dispensing devices can come in the form of separate devices which may be used independently or in combination with one another. Typically, the hair colouring or bleaching compositions are contained within separate single or multi compartment containers so that the compositions can be stored separately from one another before use. The compositions are then mixed together by a mixing means and then applied to the consumer's hair by an application means.

The most common packaging device which can be used for the present invention involves storing the developer in a container such as a bottle, tube, aerosol, or a sachet and separately storing the dye lotion in an additional compartment within the developer container or in a separate container which may be identical such as a dual sachet or aerosol systems for example or different such as a bottle and tube system.

The consumer may mix the developer lotion and the dye lotion by any means. This may simply involve the use of a mixing bowl into which the lotions are dispensed and then mixed, preferably using a mixing means such as a tool. Alternatively it may involve the addition of one of the lotions into the container of the other lotion, (typically the dye lotion is added to the developer lotion), followed by manual shaking or mixing with a tool. Another system involves the perforation or displacement of a seal located between the separate compartments of the dye and developer lotion within a single container or sachet followed by manual mixing within the container or in a separate and or additional container.

An example of such devices are the so called 'twist and go' devices. These devices allow the consumer to twist the base of a container holding the dye which enables a communication port to open that exposes the base of the bottle holding the dye and the top of the bottle holding the developer. The two components are mixed and the consumer dispenses the product by squeezing the flexible top portion of the bottle for dispensing.

Alternatively more complex devices may be utilised, whereby the lotions are mixed upon actuation of dispensing. An example of such as a complex system is a dual aerosol system e.g. bag-in-can or piston. The dye and developer are stored separately in two aerosol cans within one device, a propellant being used to pressurize the contents of the can or bag in can or piston and a valve providing the control of dispensation. When the consumer actuates the valve, the dye and developer are dispensed simultaneously out of the cans and are mixed together via a static mixer just before dispensing the product onto the hair. The ratio of the dye and developer can be manipulated by the viscosity of the products, the can pressure, or by altering the flow channel sizes through the valve. Additionally, the product can be foamed and delivered via a mousse form.

Another example of such a complex system utilises a dual piston screw system. The dye and the developer are kept in separate piston cylinder systems within the system and when the consumer actuates a button, two screws are rotated such that the dual pistons inside pressurize the liquid in the cylinders and thus force the products to move through a mixing station and out of the nozzle for dispensing. The ratios of the dye and the developer can be manipulated by the diameter of the cylinder of the package. Additionally, an in line static mixer can be used to aid mixing and such a system can be completely disposable or completely refillable.

Yet another system utilises one or more manually actuated pumps. The product may be premixed in a collapsible sachet. When the consumer actuates the pump, the liquid inside the pump is dispensed. As the manually actuated pump returns to the upright position it forces product from a collapsible sachet. Alternatively, a dual system can be installed whereby two sachets and two pumps are used to deliver the dye and the developer lotions to the hair. Alternatively, a single pump connected to two sachets can deliver the product by incorporating the mixing point within the pump. Another embodiment uses a rigid bottle and a dip tube to connect the product to the pump system. Finally, a delaminating bottle can be used in combination with a manually actuated pump where the inner layer of the bottle separates from the outer layer of the bottle which forces the contents of the bottle to be emptied.

Typically these complex systems offer the advantage of product application independently of the orientation of the product.

The devices described herein above can also be used in combination with a product delivery and or application tool to aid application of the product onto the hair. Again these devices may be of a very simple nature such as a nozzle attached to one of the containers or a separate applicator device such as a comb or brush. Such combs and brushes can be adapted in order to achieve particular effects, whether it be quick and even coverage or root/hairline touch up, or highlights or streaks. Alternatively, the container or one of the containers may be provided with a comb attached to or instead of the dispensing nozzle whereby the product is dispensed through hollow tines and dispensing apertures located in the comb tines. The comb tines may be provided with single or multiple openings along the tines to improve product application and evenness especially root to tip. Product dispensation can be achieved by mechanical pressure applied to the container for example delaminating bottles or any of the mechanisms described hereinabove. The comb may be provided on the container such as to facilitate easy application and may be positioned vertically (so called verticomb) or at an angle to allow the consumer to access all areas. All devices may be designed to have inter-changeability, so that a range of different tools for hair application can be provided to the consumer.

The application devices may also include devices which assist in achieving particular effects such as highlighting such as highlighting combs, brushes and tools, foils and highlighting caps.

Additional device technology can be used to assist in the penetration of the product into the hair. Examples of such technology include heating devices, ultraviolet light devices and ultrasound devices.

The devices and containers described hereinabove apply equally for the colour refresher component. The kits described hereinabove are well known in the art and the composition in each container can be manufactured utilizing any one of the standard approaches, these include a) 'Oil in water' process, b) 'Phase Inversion' process and c) 'One-pot' process.

The present invention also includes sequential methods of colouring hair utilizing the hair colouring kits described herein. A further embodiment of the present invention thus relates to a method of colouring the hair which is a sequential hair colouring method comprising the steps of at least two sequential treatments. The first oxidative treatment comprises the steps of:

i) providing the first individually packaged oxidising component, the second individually packaged colourant component and the third individually packaged conditioner component, ii) applying the mixture of said first and second individually packaged components to the hair and retaining said composition on the hair for a period of from 2 to 60 minutes, and subsequently optionally rinsing said composition from the hair and ii) subsequently applying said third conditioner component to the hair and retaining on the hair for a time period of 5 seconds to 10 minutes and subsequently optionally rinsing from the hair and, wherein said second colour refresher treatment comprises the steps of:

i) providing said individually packaged colour refresher component, ii) applying said component to the hair and retaining on the hair for a period of at least 3 seconds to 30 minutes and then rinsing from the hair.

According to the present invention the time period between the first and second treatment (i.e. between first oxidative and second colour refresher application) is from 1 minute to 60 days, preferably from 1 day to 31 days, more preferably from 1 to 21 days, even more preferably from 1 to 15 days. In such embodiments the time period that the first oxidative treatment composition is retained on head may be from 2 minutes to 60 minutes and preferably from 30 minutes to 45 minutes. However for compositions formulated for rapid colour delivery these time periods may be less than about 20 minutes and preferably less than about 15 minutes and most preferably for about 10 minutes. The conditioner component is preferably applied to the hair for a period of from 5 seconds to 15 minutes, preferably from 30 seconds to 10 minutes. The second colour refresher treatment of applying the second colour refresher treatment to the hair is such that application times of from 3 seconds to 30 minutes, preferably from 1 minute to 20 minutes more preferably from 3 minutes to 15 minutes most preferably from 3 to 9 minutes provide the desired colour performance. Darker shades may typically require a longer application than lighter shades.

According to the present invention the method may further comprise at least one additional first oxidative treatment(s) and or at least one additional second colour refresher treatment steps. Preferably the method includes at least 2, preferably at least 4 additional colour refresher steps prior to the application of an additional first oxidative step.

According to the present invention the method of sequential oxidative hair colouring may further comprise an additional step of applying a conditioner composition which may or may not be the same as the third individually packaged conditioner component, to the hair after the application of the colour refresher and after any subsequent additional colour refresher applications.

According to another alternative embodiment of the present invention, the method of sequential hair colouring comprises the steps of at least 2 sequential hair colouring treatments wherein the time period between each treatment is less than 14 days, wherein said first treatment comprises the steps of:

i) providing a first individually packaged oxidising component comprising at least one oxidising agent, a second individually packaged colourant component comprising at least one oxidative dye or at least one alkalising agent and a third individually packaged conditioner component comprising a conditioning agent ii) applying a mixture of said first and second individually packaged components to the hair and retaining said composition on the hair for a period of from 2 to 60 minutes, and optionally subsequently rinsing said composition from the hair and iii) —subsequently applying said third conditioner component to the hair and retaining said composition on the hair for a time period of from 5 seconds to 10 minutes and optionally subsequently rinsing said composition from the hair, and wherein said second treatment comprises the steps of:

i) providing said individually packaged colour refresher component comprising at least one preformed dye or water soluble or water dispersible dye, ii) applying said colour refresher component to the hair and retaining said composition on the hair for a time period of less than 10 minutes and then rinsing said composition from the hair.

Test Methods

Interfacial Tension Measurement Protocol

The silicone/water interfacial tensions of the functionalized silicones were measured via pendant drop shape analysis on a Kruss DSA-10 instrument as taught in F. K. Hansen, G. Rodsrun, "Surface tension by pendant drop. A fast standard instrument using computer image analysis", Journal of Colloid and Interface Science, Volume 141, Issue 1, January 1991, pages 1-9. The accuracy of this method is dependent upon the density difference between the reference fluid (usually water) and the test fluid. Given that many of the present functionalized silicones have densities approaching that of water, $D_2O$ (with a density of 1.1 g/cm$^3$) was substituted for $H_2O$ as the more dense phase, in order to ensure a sufficient density difference. The respective densities of the functionalized silicones were measured with a Calculating Precision Density Meter DMA 55 instrument from Apollo Scientific Limited. This analysis is performed at room temperature, 18 to 25° C., with no differences in values observed for silicone fluids within this range of temperature.

Viscosity of Functionalized Silicone Fluids—Measurement Protocol

An AR 500 rotational rheometer (TA Instruments Ltd., Leatherhead, Surrey KT22 7UQ, UK) is used to determine the viscosity of the functionalized silicone fluids used herein. The determination is performed at 30° C., with the 4 cm 2° steel cone measuring system set with a 49 μm (micron) gap and is performed via the programmed application of a shear stress of 0.5 to 590 Pa over a 2 minute time period. These data are used to create a shear rate vs. shear stress curve for the material. This flow curve can then be modelled in order to provide a material's viscosity. These results were fitted with the following well-accepted Newtonian model:

$$\text{Viscosity}, \mu = \sigma/\gamma$$

(where σ is shear stress; γ is shear rate)

Viscoelasticity measurement of silicone/durability active blends.

The AR500 raotational Rheometer (TA Instruments) is used to determine the G' and G" of the functional silicone fluids mixed with durability additives used herin. The determination is performed at 25° C., with the 6 cm acrylic parallel plate measuring system set with a 100 micron gap and is performed via the programmed application of a oscillatory stress of 2 Pa over a oscillation frequency range of 1 to 40 Hz. This data is used to determine the ration of G' to G". A minimum of 30 data points is recorded over a linear frequency ramp. This data is used to determine the mean ratio of G' to G" between 20 and 40 Hz.

Method for Assessing Silicone Particle Size Within a Product

A microscope (Nikon Eclipse E800) is utilised to determine the silicone particle size in the final product. Typically, pictures are taken (JVC color video camera KY-F50) of the final product at a magnification ranging from 100× to 400×. Using the captured image a scale is superimposed (Image software—Lucia G Version 4.51 (build 028), Laboratory Imaging) previously calibrated using a 100 μm Graticule (Graticules Ltd, Tonbridge Wells, Kent, England) and compared to the average silicone particle within the sample to provide an estimation of particle size.

EXAMPLES

The following examples illustrate the hair colouring kits and compositions according to the present invention. It is understood that the examples and embodiments described herein are for illustrative purposes only and that various modifications or changes in light thereof will be suggested to one skilled in the art without departing from the scope of the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Example formulations of each of the components of the present invention are given below. The oxidative dyes utilized in the colourant component and the preformed dyes used in the colour refresher component as part of a kit or as an individual component are selected so as to provide a consistent colour for the consumer when utilized in combination.

| Ingredients | Colourant component | | | | | |
|---|---|---|---|---|---|---|
| | #1 | #2 | #3 | #4 | #5 | #6 |
| Water qs to 100% | | | | | | |
| Steareth-21 | 3 | 3 | 3 | 3 | 3 | 3 |
| Cocamide MEA | 4 | 4 | 4 | 4 | 4 | 4 |
| Sodium sulfite | 0.1 | 0.1 | 0.1 | 0.1 | 0.1 | 0.1 |
| EDTA | 0.1 | 0.1 | 0.1 | 0.1 | 0.1 | 0.1 |
| Erythorbic acid | 0.4 | 0.4 | 0.4 | 0.4 | 0.4 | 0.4 |
| P-phenylenediamine | 0.3 | 0.3 | 0.3 | 0.3 | 0.3 | 0.3 |
| P-aminophenol | 0.2 | 0.2 | 0.2 | 0.2 | 0.2 | 0.2 |
| 2-methylresorcinol | 0.5 | 0.5 | 0.5 | 0.5 | 0.5 | 0.5 |
| 4-amino-2-hydroxytoluene | 0.2 | 0.2 | 0.2 | 0.2 | 0.2 | 0.2 |
| Sodium sulphate | 1 | 1 | 1 | 1 | 1 | 1 |
| C12-15 Pareth-3 | 9 | 9 | 9 | 9 | 9 | 9 |
| Dilinoleic acid | 2 | 2 | 2 | 2 | 2 | 2 |
| Fragrance | 1 | 1 | 1 | 1 | 1 | 1 |
| Ammonium hydroxide | 7.5 | 7.5 | 7.5 | 7.5 | — | — |
| Ammonium Carbonate | — | — | — | — | 10.0 | 10.0 |
| Sodium metasilicate | 0.2 | 0.2 | 0.2 | 0.2 | 0.2 | 0.2 |
| Behentrimonium chloride | 3 | 3 | 3 | 3 | 3 | 3 |
| Oleth-10 | 5 | 5 | 5 | 5 | 5 | 5 |
| Linoleamidopropyl dimethylamine dimmer dilinoleate | 4 | 4 | 4 | 4 | 4 | 4 |
| Polyquaternium-22 | 1 | 0.5 | 1 | 0 | 1 | 0 |
| Sodium Glycinate | — | — | — | — | — | 5.0 |

| | Oxidizing component | | | | | |
|---|---|---|---|---|---|---|
| | #1 | #2 | #3 | #4 | #5 | #6 |
| Water | qs to 100% | qs to 100% | qs to 100% | qs to 100% | qs to 100% | qs to 100% |
| Hydrogen peroxide (35% active) | 17.5 | 17.5 | 17.5 | 17.5 | 17.5 | 17.5 |
| Laureth-23 | 0.5 | 0.5 | 0.5 | 0.5 | 0.5 | 0.5 |

-continued

| | Oxidizing component | | | | | |
|---|---|---|---|---|---|---|
| | #1 | #2 | #3 | #4 | #5 | #6 |
| Etidronic acid | 0.01 | 0.01 | 0.01 | 0.01 | 0.01 | 0.01 |
| Cetearyl alcohol and ceteareth-20 | 2.0 | 2.0 | 2.0 | 2.0 | 2.0 | 2.0 |
| Styrene/PVP copolymer | 0.5 | 0.5 | 0.5 | 0.5 | 0.5 | 0.5 |
| Steareth-21 | 0.5 | 0.5 | 0.5 | 0.5 | 0.5 | 0.5 |
| Polyquaternium-37 | 0 | 0 | 0.5 | 0.5 | 0.5 | 0.5 |
| Polyquaternium-22 | 0 | 0.5 | 0 | 1 | 0 | 1 |
| pH of final mix | 10.0 | 10.0 | 10.0 | 10.0 | 10.0 | 10.0 |

| Ingredient | Conditioner Component | | | |
|---|---|---|---|---|
| | #1 | #2 | #3 | #4 |
| Demineralised water | qs to 100 | qs to 100 | qs to 100 | qs to 100 |
| Cetyl alcohol | 2.3 | 2.3 | 4.0 | 4.0 |
| Stearyl alcohol | 2.3 | 2.3 | 2.0 | 2.0 |
| Ceteareth-25 | 1.5 | 1.5 | — | — |
| Phonoxyethanol | 0.1 | 0.1 | 0.3 | 0.3 |
| Sodium benzoate | 0.1 | 0.1 | — | — |
| Tetrasodium EDTA (87%) | 0.1 | 0.1 | 0.1 | 0.1 |
| Stearamidopropyl-dimethyamine | — | — | 1.6 | 2.0 |
| L-Glutamic acid | — | — | 0.5 | 0.7 |
| Dicetyldimonium chloride | — | — | 0.5 | — |
| Benzyl alcohol | — | — | 0.3 | — |
| (Silicone Premix) | (5.000) | (5.000) | (3.000) | (7.000) |
| Aminofunction silicone sold under the name Wacker Belsil ADM1100 by the company Wacker Chemie | 4.995 | — | — | 7.000 |
| Aminofunctional silicone sold under the name TSF4707 by GE Bayer Silicone | — | 5.000 | 2.995 | — |
| MQ resin sold under the name SR1000 by the company GE Bayer Silicones | 0.005 | — | 0.005 | — |

| Ingredient | Colour refresher component: shampoo | | |
|---|---|---|---|
| | #1 | #2 | #3 |
| Aqua | qs | qs | qs |
| Sodium laureth sulphate | 10 | 10 | 10 |
| Peg-3 distearate | 2 | 2 | 2 |
| Cocoamidopropyl betaine | 4 | 4 | 4 |
| PEG-200 Hydrogenated glceryl palmate | 1 | 1 | 1 |
| Denat. alcohol1.90000 | 2 | 2 | 2 |
| Sodium chloride | 1 | 1 | 1 |
| Phenoxyethanol | 0.5 | 0.5 | 0.5 |
| Methyl paraben | 0.2 | 0.2 | 0.2 |
| Propylparaben | 0.1 | 0.1 | 0.1 |
| Perfume | 0.3 | 0.3 | 0.3 |
| HC Blue #2 | 0.2 | 0.2 | 0.3 |

-continued

| | Colour refresher component: shampoo | | |
|---|---|---|---|
| Ingredient | #1 | #2 | #3 |
| HC Red #10 | 0.09 | — | 0.2 |
| HC Red #11 | 0.03 | — | — |
| Hhydroxyethyl-2-Nitro-P-toluidine | 0.1 | — | — |

| | | Color Refresher Cream | |
|---|---|---|---|
| Ingredient | Chemical Name | Dark Brown shade WT. % | Light Brown shade WT. % |
| 1 | Aminomethyl Propanol | 1.5 | 2.5 |
| 2 | Diethylene Glycol Monoethyl Ether | 4 | 4 |
| 3 | PEG-50 Palm Amide | 2 | 2 |
| 4 | Lauryl Polyglucose * | 1 | 1 |
| 5 | Erythorbic Acid | 0.025 | 0.025 |
| 6 | HC Yellow No. 2 | 0.16 | 0.02 |
| 7 | Disperse Black 9 | 0.02 | 0.02 |
| 8 | HC Red No. 3 | 0.1 | 0.0113 |
| 9 | Disperse Violet 1 | 0.1 | — |
| 10 | HC Blue No. 2 | 0.9 | 0.1 |
| 11 | Disperse Blue 377 | 0.23 | 0.01 |
| 12 | HC Orange No. 1 | 0.0126 | 0.01 |
| 13 | Deionized Water | QS | QS |
| 14 | Citric Acid | 0.5 | 0.5 |
| 15 | Isopropyl Alcohol | 0.8 | — |
| 16 | Hydroxyethylcellulose * | 0.9 | — |
| 17 | Carbomer * | — | 0.55 |
| 18 | Trimethylsilylamodimethicone * | 2 | 2 |
| 19 | Fragrance 50854M | 1 | 1 |
| 20 | Glycerin | 0.2 | 0.2 |
| 21 | Hydrolyzed Whole Wheat Protein | 0.1 | 0.1 |

* Lauryl Polyglucose: trade name is Plantaren 1200N from Cognis
* Hydroxyethylcellulose: trade name is Natrosol from Hercules
* Carbomer: trade name is Carbopol Ultrez 10 Polymer from Noveon
* Trimethylsilylamodimethicone is conditioning additive Q2-8220 from Dow Corning All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are the scope of this invention.

What is claimed is:

1. A hair colouring kit comprising:
   i) a first individually packaged oxidising component comprising from about 0.1% to about 10% of at least one oxidising agent,
   ii) a second individually packaged colourant component comprising from about 0.001% to about 10% of at least one oxidative dye or at least one alkalising agent or mixtures thereof,
   iii) a third individually packaged conditioner component comprising from about 0.1% to about 20% of a functionalized amino silicone according to the formula:

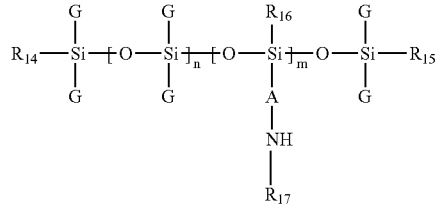

wherein, m and n are numbers with a sum (n+m) ranging from 2 to 2000, n is a number ranging from 1 to 1999, and m is a number ranging from 1 to 1999;
   and m and n are selected wherein the ratio of m:n is from 1:1000 to 1:10, R14, R15, R16, which may be identical or different, are selected from a hydroxyl radical, C1-C4 alkoxy radicals and methyl radicals,
   A is selected from linear and branched C3-C8 alkenyl radicals,
   R17 is selected from H, phenyl, linear or branched C1-C4 alkyl radical, benzyl or linear or branched (C2-C8)NH2 groups,
   G is selected from H, phenyl, hydroxyl, C1-C8 alkyl, and
   wherein said aminosilicone is of the random type or block type, and
   iv) a fourth individually packaged colour refresher component comprises from about 0.01% to about 10% of said at least one preformed dye, water soluble or water dispersible dye.

2. A hair colouring kit according to claim 1, wherein said fourth individually packaged colour refresher component further comprises a surfactant, and or a conditioning agent.

3. A hair colouring composition comprising
   i) a colour refresher component comprising at least one preformed or water soluble or water dispersible dye and
   ii) a conditioning agent comprising a functionalized amino silicone according to the formula:

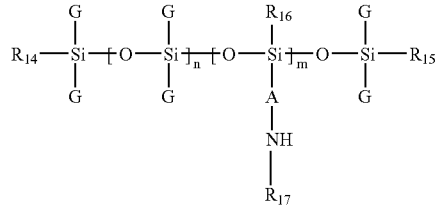

wherein, m and n are numbers with a sum (n+m) ranging from 2 to 2000, n is a number ranging from 1 to 1999, and m is a number ranging from 1 to 1999; and
   wherein m and n are selected such that ratio of m:n is from 1:1000 to 1:10, R14, R15, R16, which may be identical or different, are selected from a hydroxyl radical, C1-C4 alkoxy radicals and methyl radicals,
   A is selected from linear and branched C3-C8 alkenyl radicals, R17 is selected from H, phenyl, linear or branched C1-C4 alkyl radical, benzyl or linear or branched (C2-C8)NH2 groups, G is selected from H, phenyl, hydroxyl, C1-C8 alkyl, preferably methyl, and wherein said aminosilicone is the random type or block type.

4. A method of sequential hair colouring comprising the steps of at least two sequential hair colour treatments, wherein the time period between each treatment is from about 1 minute to about 60 days, wherein said first colouring treatment comprises the steps of:
  i) providing said first individually packaged oxidising component, said second individually packaged colourant component and said third individually packaged conditioner component according to claim 1,
  ii) applying a mixture of said first and second individually packaged components to the hair and retaining said composition on the hair for a period of from about 2 minutes to about 60 minutes, and subsequently rinsing said composition from the hair,
  iii) subsequently applying said third conditioner component to the hair and retaining said component composition on the hair for a time period of from about 5 seconds to about 15 minutes, wherein said second coloring treatment comprises the steps of:
  i) providing said individually packaged colour refresher component according to claim 1,
  ii) applying said colour refresher component to the hair and retaining said component composition on the hair for a time period of at least about 3 seconds to about 30 minutes.

5. A method of sequential hair colouring according to claim 4, wherein said method further comprises the step of applying a conditioner composition to the hair after the application of said colour refresher component.

6. A method of sequential hair colouring according to claim 4, wherein said method further comprises the additional step of applying at least one additional first oxidative hair colouring treatment and or at least one additional second colour refresher treatment.

7. A method of sequential hair colouring according to claim 4, wherein the time period between each treatment is from about 1 day to about 21 days.

8. A method of sequential hair colouring according to claim 4, wherein said individually packaged colour refresher component is applied to the hair and retained on the hair for a period of from about 3 seconds to about 30 minutes.

9. A method of sequential hair colouring comprising the steps of at least 2 sequential hair colouring treatments wherein the time period between each treatment is less than about 14 days, wherein said first treatment comprises the steps of:
  i) providing a first individually packaged oxidising component comprising at least one oxidising agent, a second individually packaged colourant component comprising at least one oxidative dye or at least one alkalising agent or mixtures thereof and a third individually packaged conditioner component comprising a conditioning agent according to claim 1,
  ii) applying a mixture of said first and second individually packaged components to the hair and retaining said component composition on the hair for a period of from about 2 to about 60 minutes, and subsequently rinsing said composition from the hair and
  iii) subsequently applying said third conditioner component to the hair and retaining said composition on the hair for a time period of from about 5 seconds to about 10 minutes and subsequently rinsing said composition from the hair, and wherein said second treatment comprises the steps of:
  i) providing said individually packaged colour refresher component comprising at least one preformed or water soluble or water dispersible dye,
  ii) applying said colour refresher component to the hair and retaining said composition on the hair for a time period of less than about 10 minutes and then rinsing said composition from the hair.

* * * * *